United States Patent [19]
Wierzbicki et al.

[11] Patent Number: 5,792,789
[45] Date of Patent: *Aug. 11, 1998

[54] ACIDS AND ESTERS OF DIOSMETIN

[75] Inventors: Michel Wierzbicki, L'Etang la Ville; Marie-Francoise Boussard, Mareil sur Mauldre; Tony Verbeuren, Vernouillet; Marie-Odile Vallez, Champs sur Marne, all of France

[73] Assignee: Adir et Compagnie, Courbevoie, France

[ * ] Notice: The term of this patent shall not extend beyond the expiration date of Pat. No. 5,629,339.

[21] Appl. No.: 842,988

[22] Filed: Apr. 25, 1997

[30] Foreign Application Priority Data

Apr. 25, 1996 [FR] France ............... 96.05247

[51] Int. Cl.$^6$ ............... A61K 31/35; C07D 311/30
[52] U.S. Cl. ............... 514/456; 549/403
[58] Field of Search ............... 549/403; 514/456

[56] References Cited

U.S. PATENT DOCUMENTS

| | | | |
|---|---|---|---|
| 2,350,804 | 6/1944 | Ohta | 549/403 |
| 2,897,211 | 7/1959 | Da Re | 549/403 |
| 3,219,531 | 11/1965 | Blaise | 549/403 |
| 5,629,339 | 5/1997 | Wierzbicki et al. | 514/456 |

OTHER PUBLICATIONS

Angiology 48, No. 7, 559–567 (1997).
Simpson, Sci. Proc. Royal Dublin Soc., vol. 27, pp. 111–117 1956.

*Primary Examiner*—Bernard Dentz
*Attorney, Agent, or Firm*—The Firm of Gordon W. Hueschen

[57] ABSTRACT

Acids and esters of diosmetin of formula:

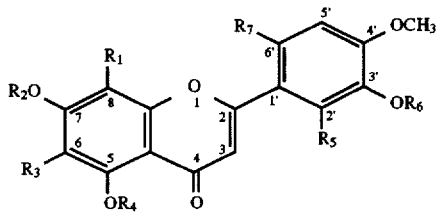

wherein $R_1$, $R_2$, $R_3$, $R_4$, $R_5$, $R_6$ and $R_7$ are as defined in the description, and the physiologically tolerable salts thereof.

The said compounds can be used as medicaments in the treatment of chronic venous insufficiency and any other disorder involving hyperpermeability and/or inflammation.

6 Claims, No Drawings

ACIDS AND ESTERS OF DIOSMETIN

The present invention relates to new acids and esters of diosmetin and to pharmaceutical compositions containing them.

It relates more especially to compounds of formula (I):

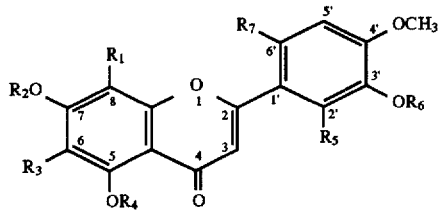

wherein:

$R_2$, $R_4$ and $R_6$, which are identical or different, each represents a hydrogen atom, an alkyl radical having from 1 to 5 carbon atoms in straight or branched chain, or a radical of formula:

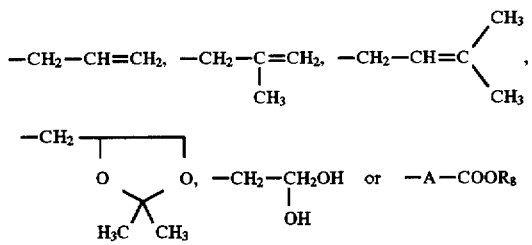

wherein:

A represents a straight hydrocarbon chain having from 1 to 3 carbon atoms and optionally substituted by a methyl radical, or by a hydroxy radical;

$R_8$ represents a hydrogen atom or an alkyl radical having from 1 to 5 carbon atoms and $R_3$ and $R_5$, which are identical or different, each represents a hydrogen atom or a radical of formula:

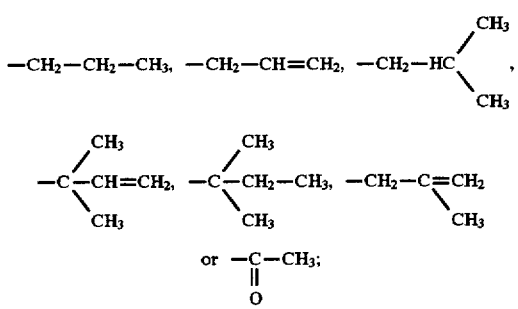

and $R_1$ and $R_7$, which are identical or different, each represents a hydrogen atom or a radical of formula:

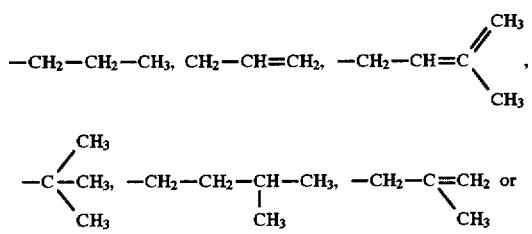

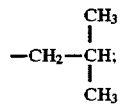

with the proviso that:
if 1 or 2 of the substituents $R_2$, $R_4$ and $R_6$ represent(s) the group —A—$COOR_8$ wherein A and $R_8$ are as defined above,
then at least one of the remaining substituents among $R_1$ to $R_7$ does not represent a hydrogen atom;

and also to the enantiomers thereof, where they exist, and to the physiologically tolerable salts thereof with appropriate bases.

The prior art is illustrated especially by the European patent application 0 319 412, corresponding to U.S. Pat. No. 4,970,301, which relates to substituted 2-piperazinyl-2-oxoethylene flavonoid compounds, which can be used in the treatment of vascular disorders.

The ever-increasing proliferation of those disorders warrants a favourable welcome to any invention of medicaments in that field. It is within that framework that the present invention is presented, relating to a family of products of chemical structures well differentiated from those of hitherto known active ingredients, and having pharmacological and therapeutic properties especially valuable in the treatment of the said disorders.

The presence of a specific venous capillary microangiopathy has been demonstrated in chronic venous insufficiencies. That microangiopathy, which is the result of venous hypertension, leads to venous capillary filtration disorders (hyperpermeability) and thus micro-oedemas (Barbier et al., La Presse Médicale, 23: p 213–224, 1994). The improvement of microcirculatory disorders that accompany chronic venous insufficiency (oedema, inflammation) should form part of the medicament treatment of that disorder (Chauveau, La Presse Médicale, 23: p. 243–249, 1994).

It has now been found, by the Applicant, that the compounds of the present invention have an anti-hyperpermeability activity, which has been demonstrated using modern microscopy techniques to evaluate the responses of the microcirculation, see Bjork et al., Progr. Appl. Microcircul., 6, 41–53, (1984). Thus, the compounds of the present invention can be used in particular in the treatment of chronic venous insufficiency and in any other disorder involving hyperpermeability and/or inflammation.

The present invention relates also to pharmaceutical compositions comprising as active ingredient a compound of formula I or a physiologically tolerable salt thereof, in admixture or association with one or more appropriate pharmaceutical excipients.

The pharmaceutical compositions so obtained are generally in dosage form containing from 1 to 500 mg of active ingredient. They may, for example, be in the form of tablets, dragees, gelatin capsules, suppositories or injectable or drinkable solutions and may be administered by the oral, rectal or parenteral route.

The dosage may vary, especially in accordance with the age and weight of the patient, the administration route, the nature of the disorder and associated treatments, and ranges from 1 to 500 mg of active ingredient from 1 to 6 times per day.

The compounds of formula I are all prepared from known starting materials using conventional methods that, depending on the case in question, employ, for example, reactions selected from alkylation, reduction, transposition, rearrangement, hydrolysis and esterification reactions, as illustrated on sheets 1 to 8.

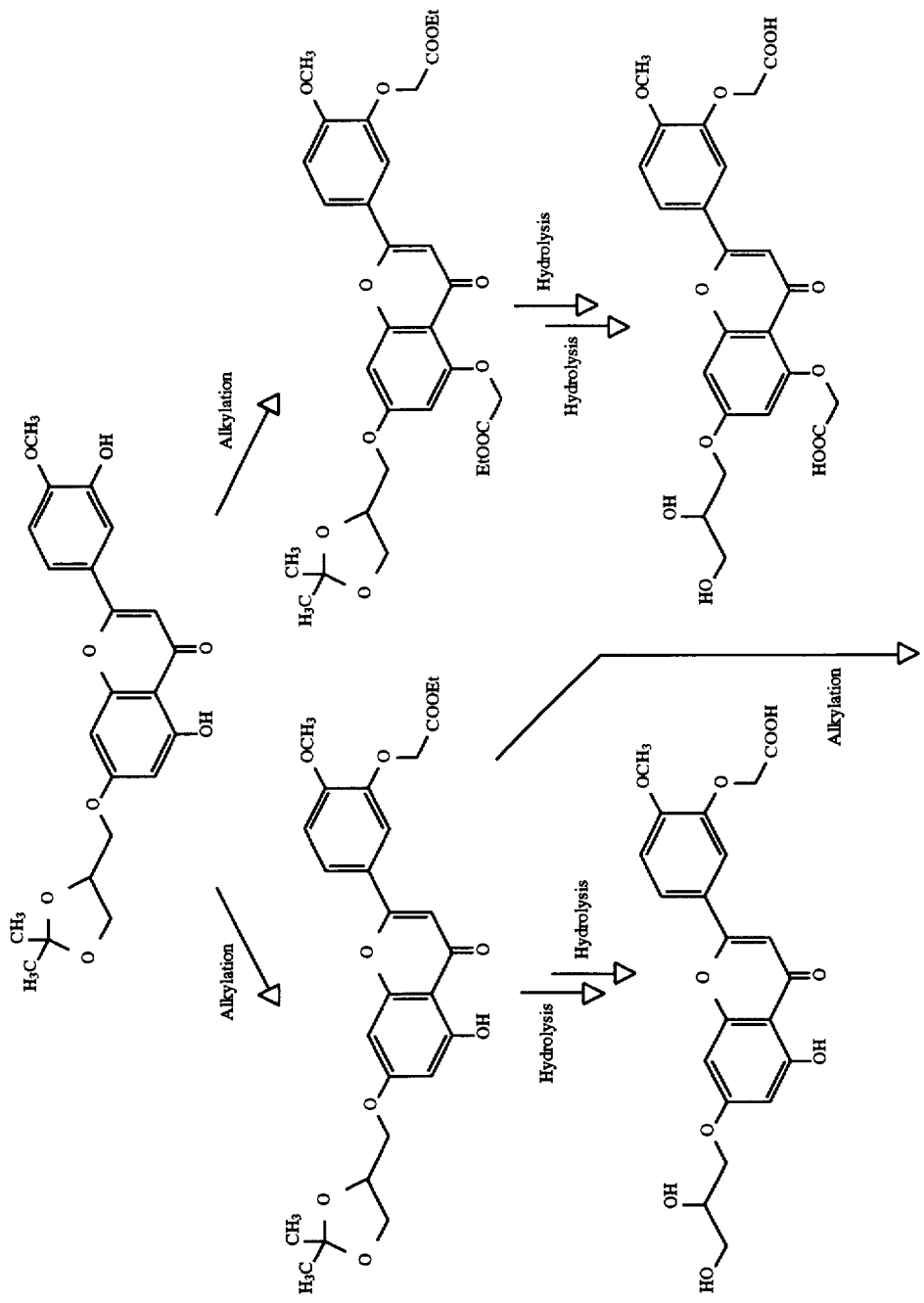

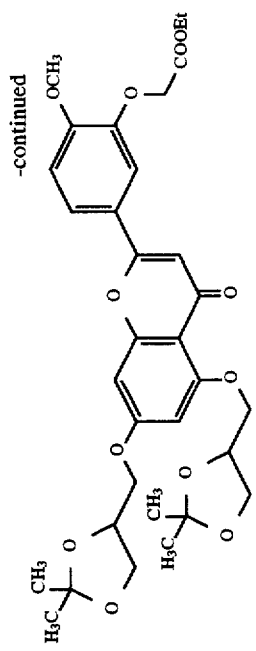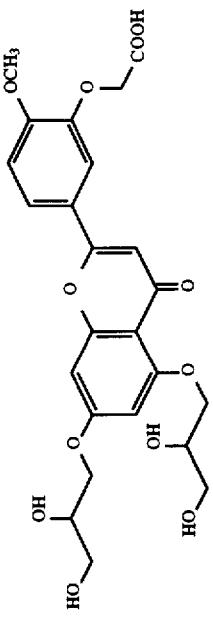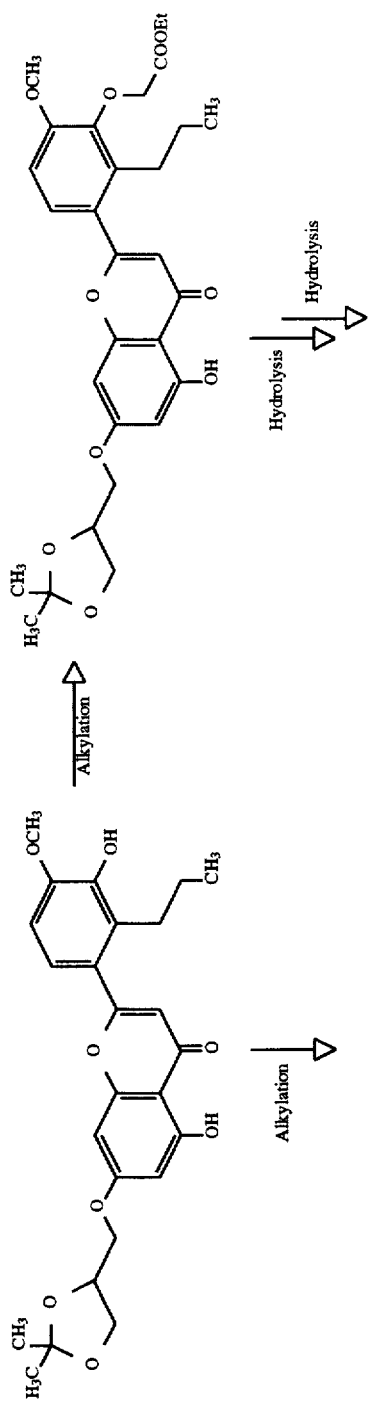

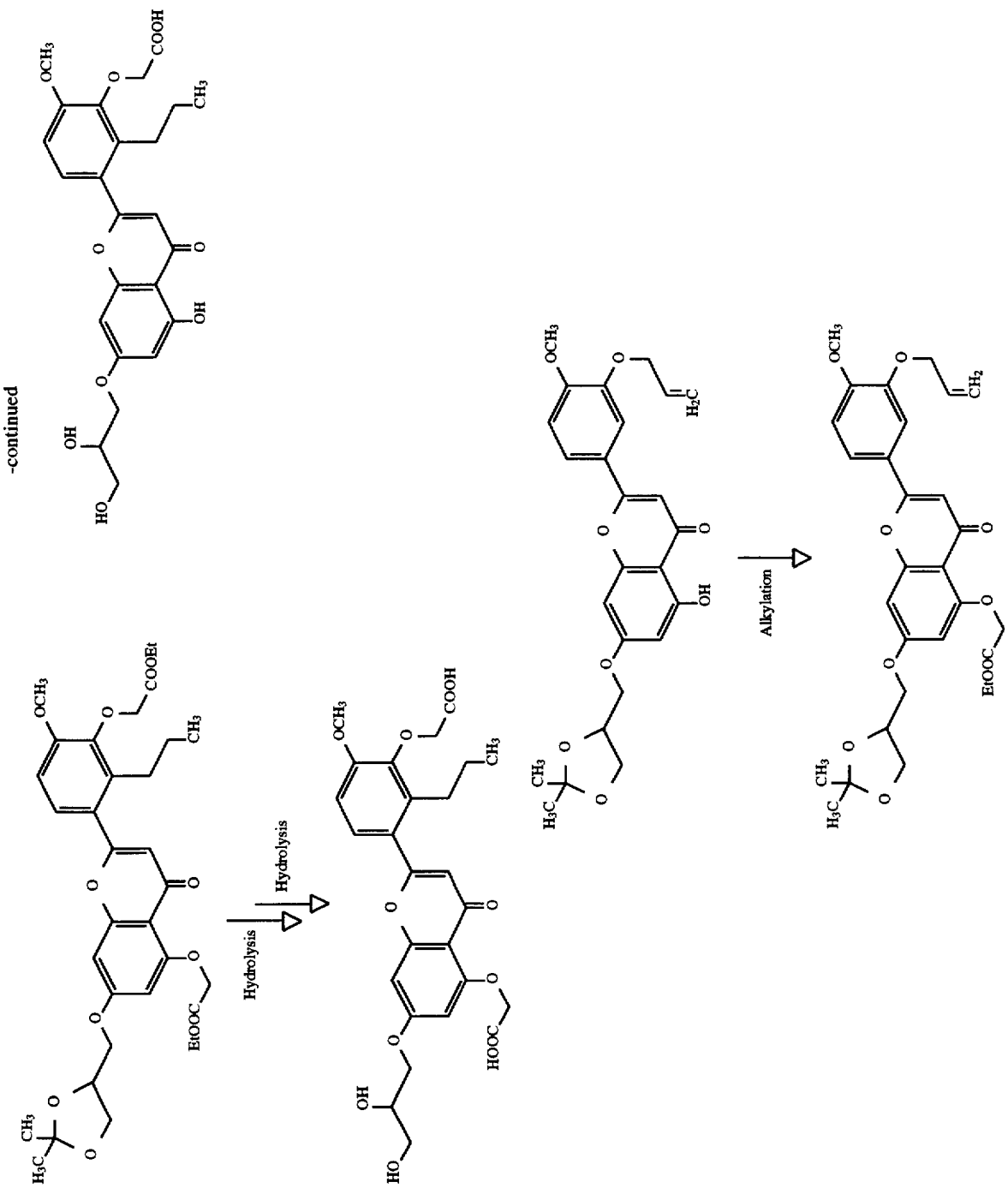

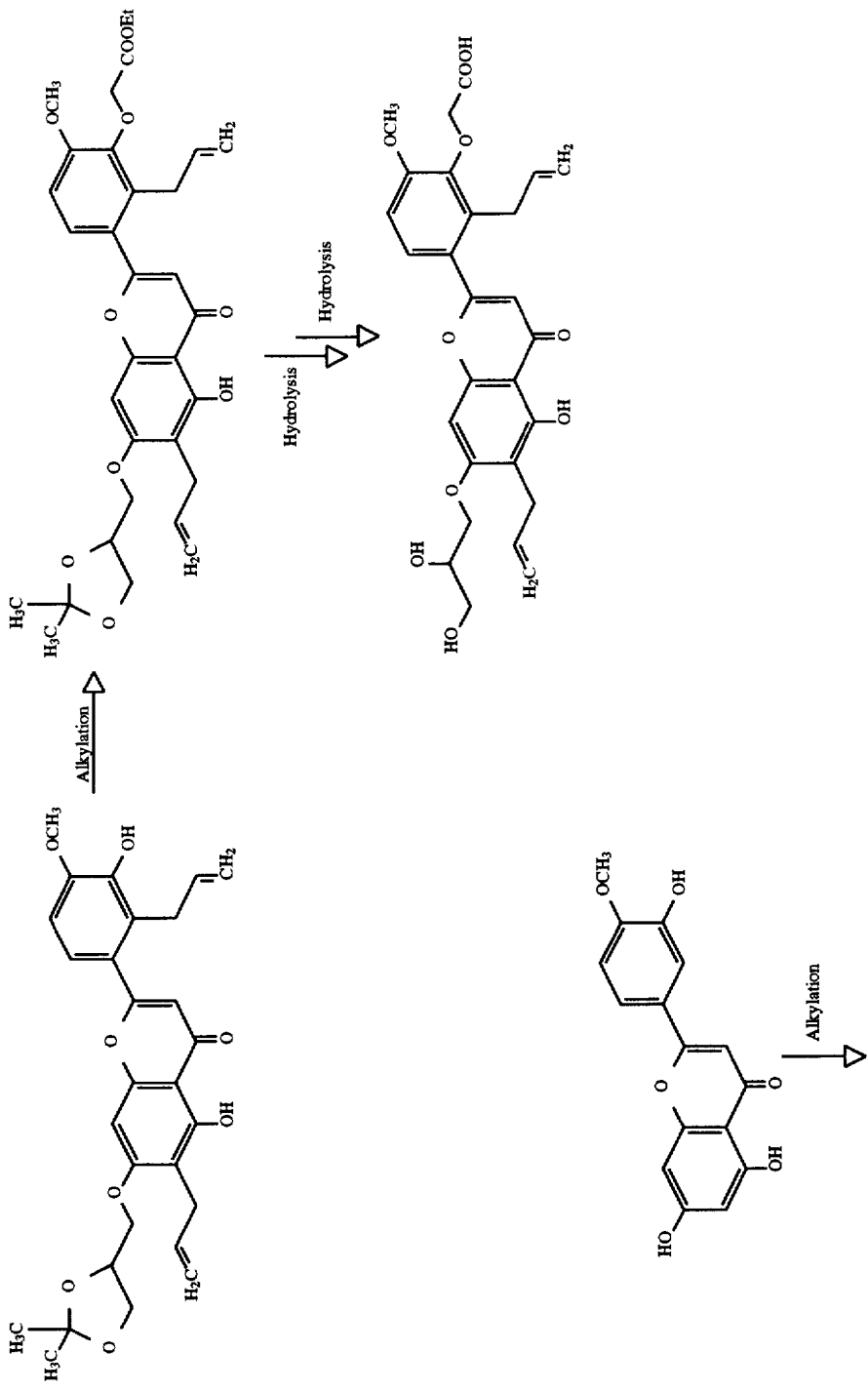

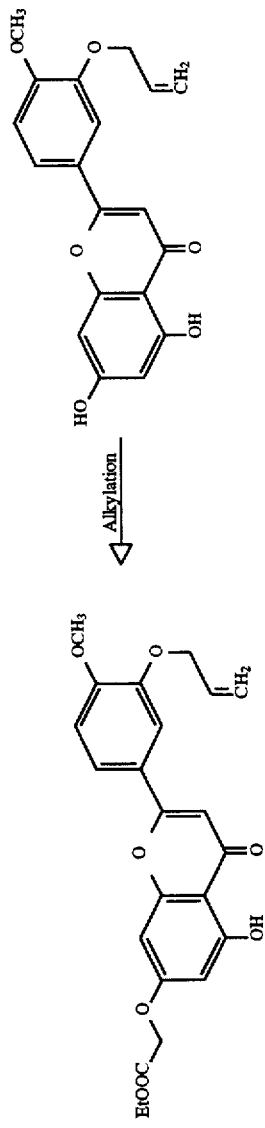
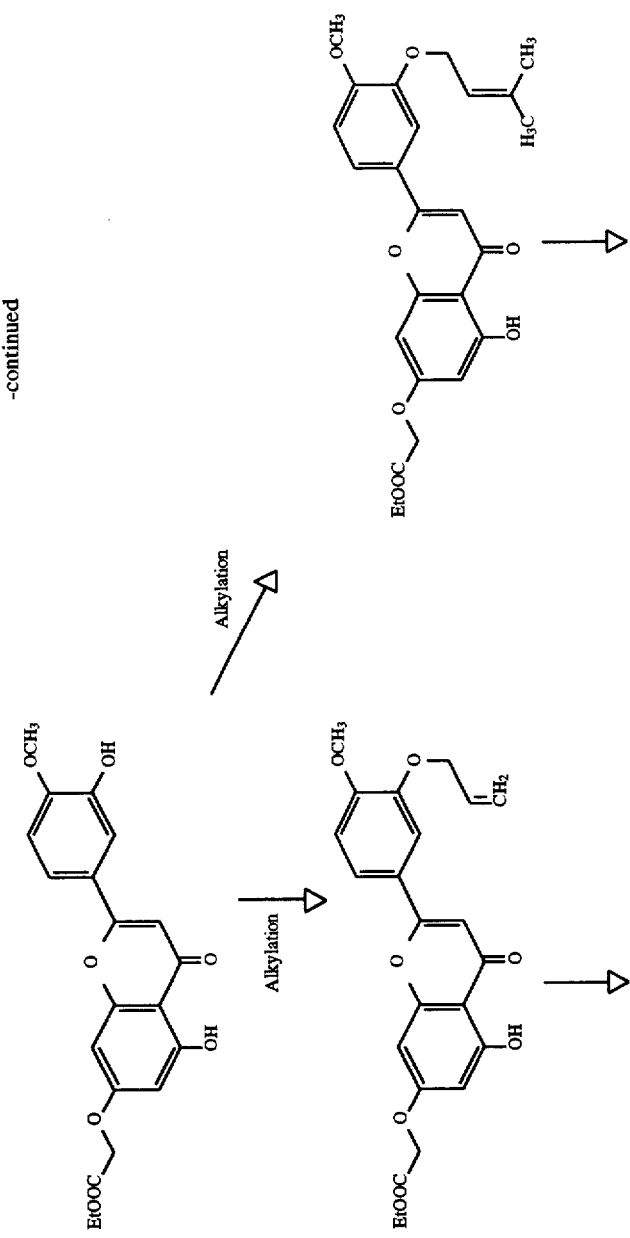

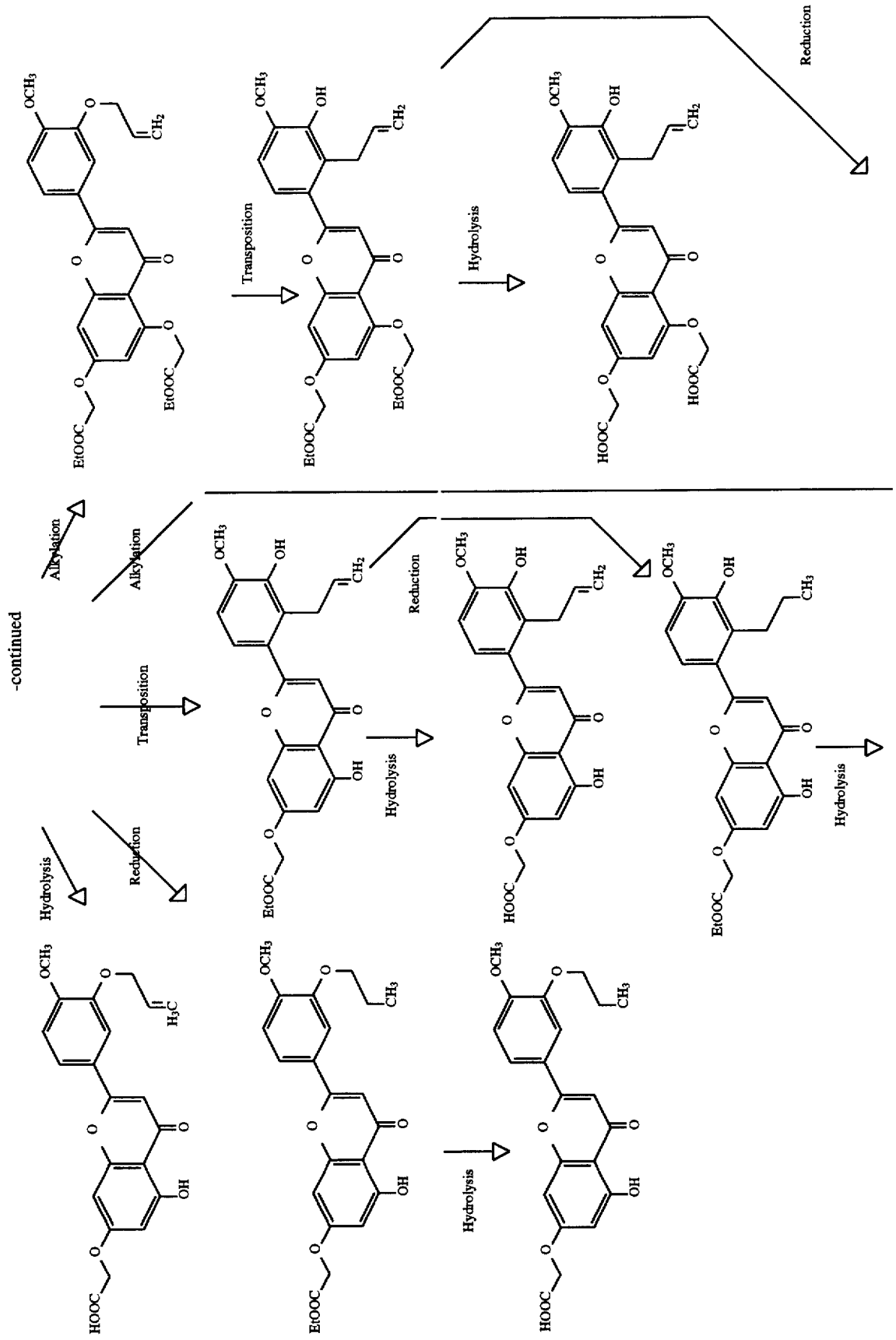

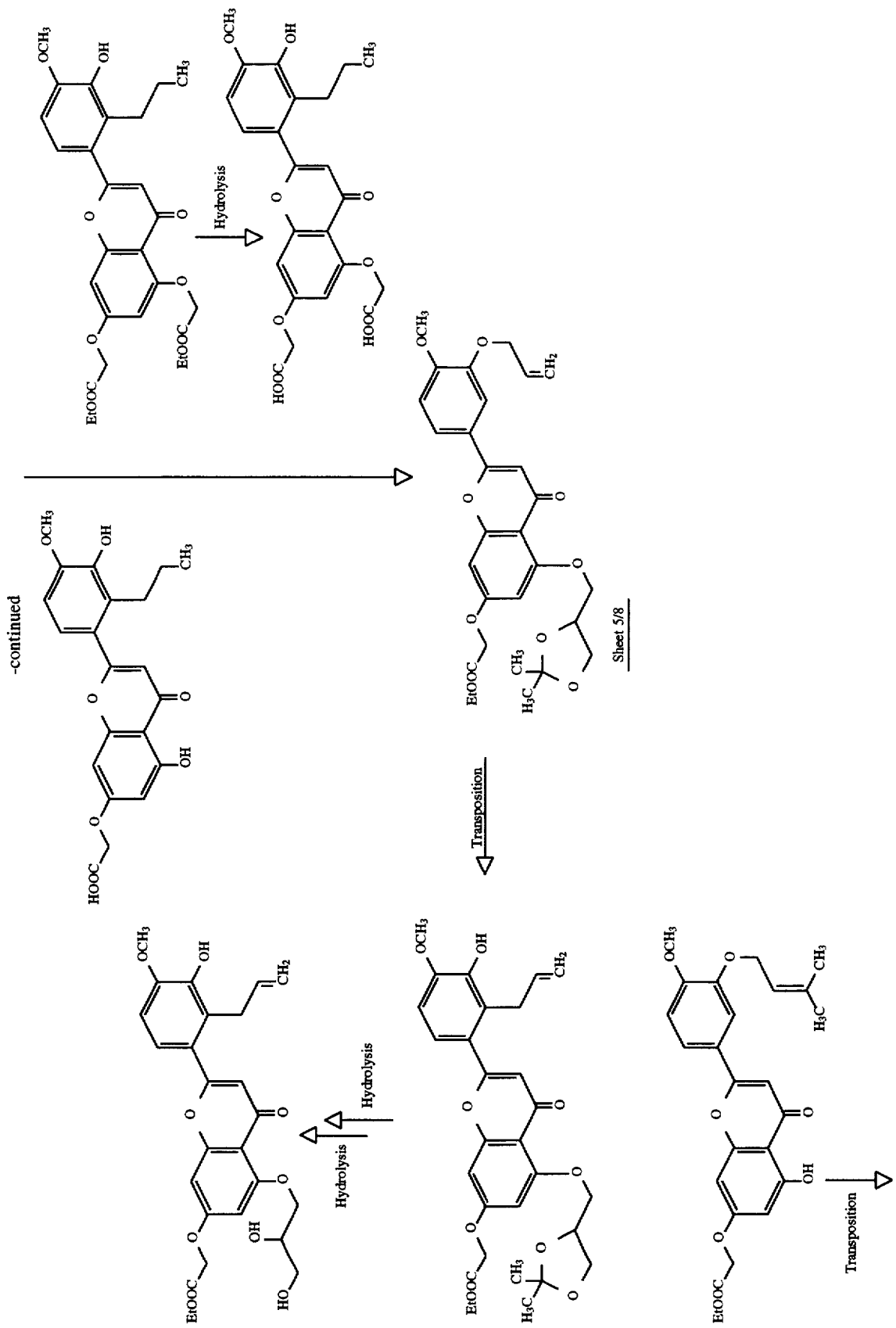

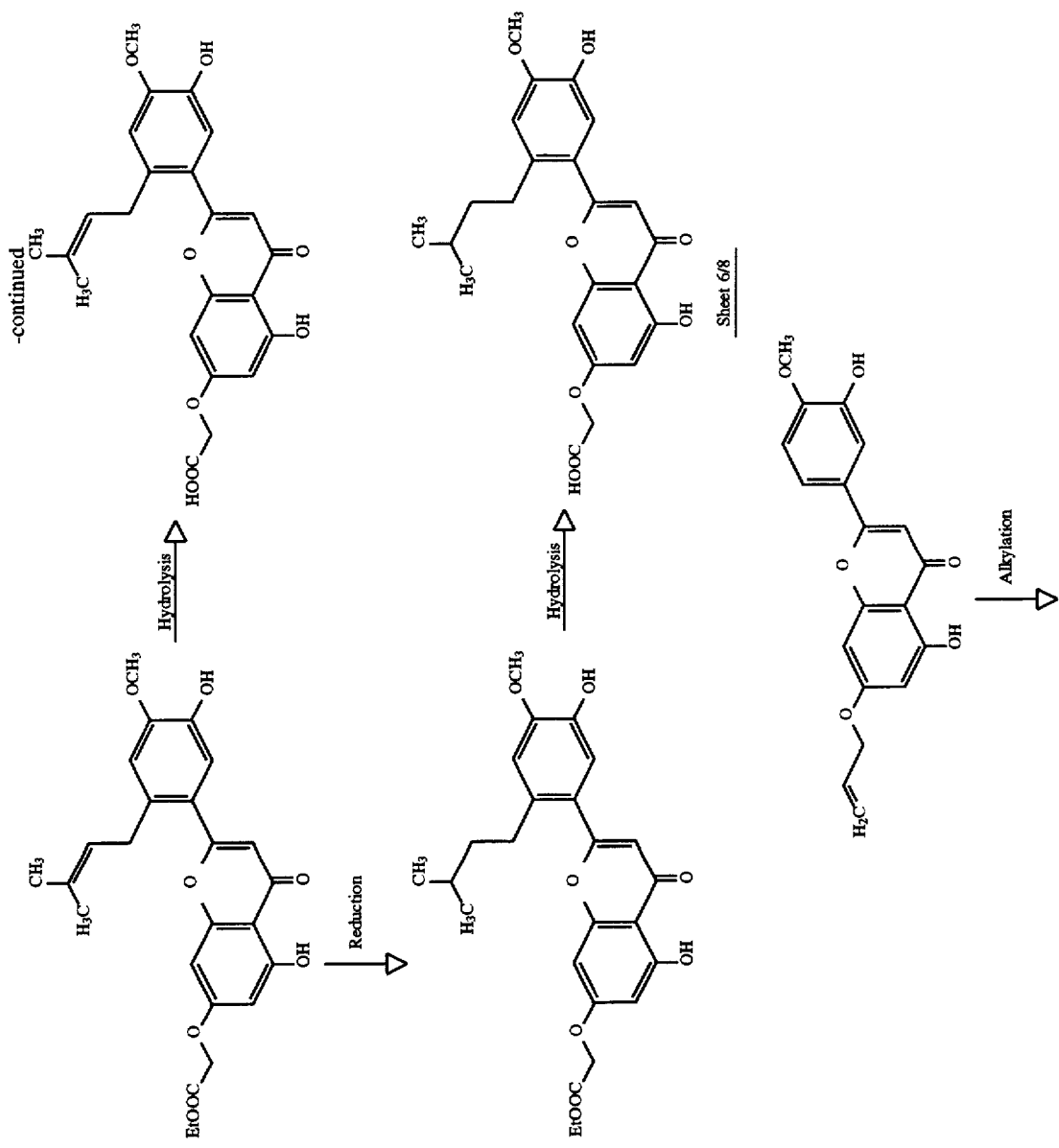

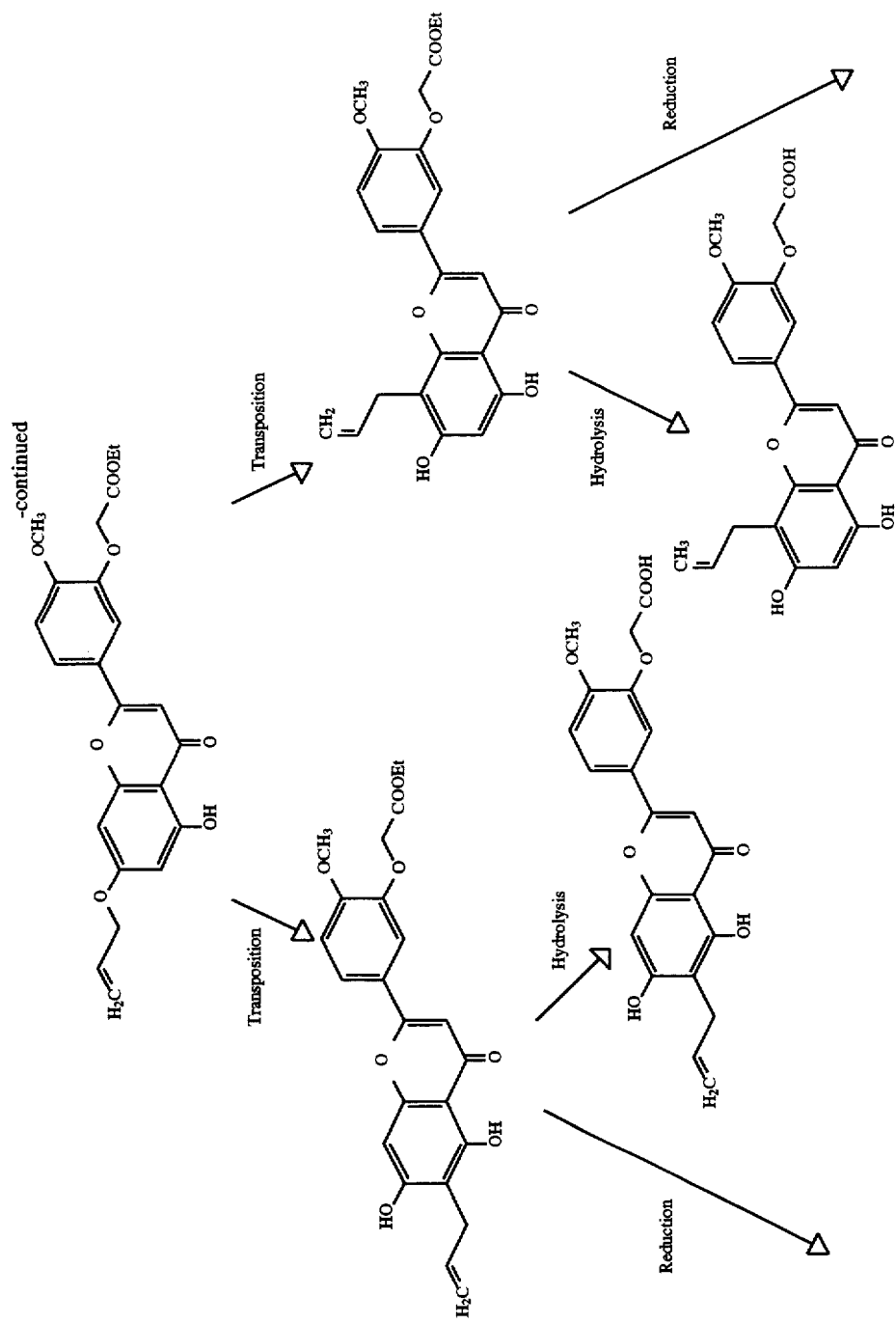

-continued
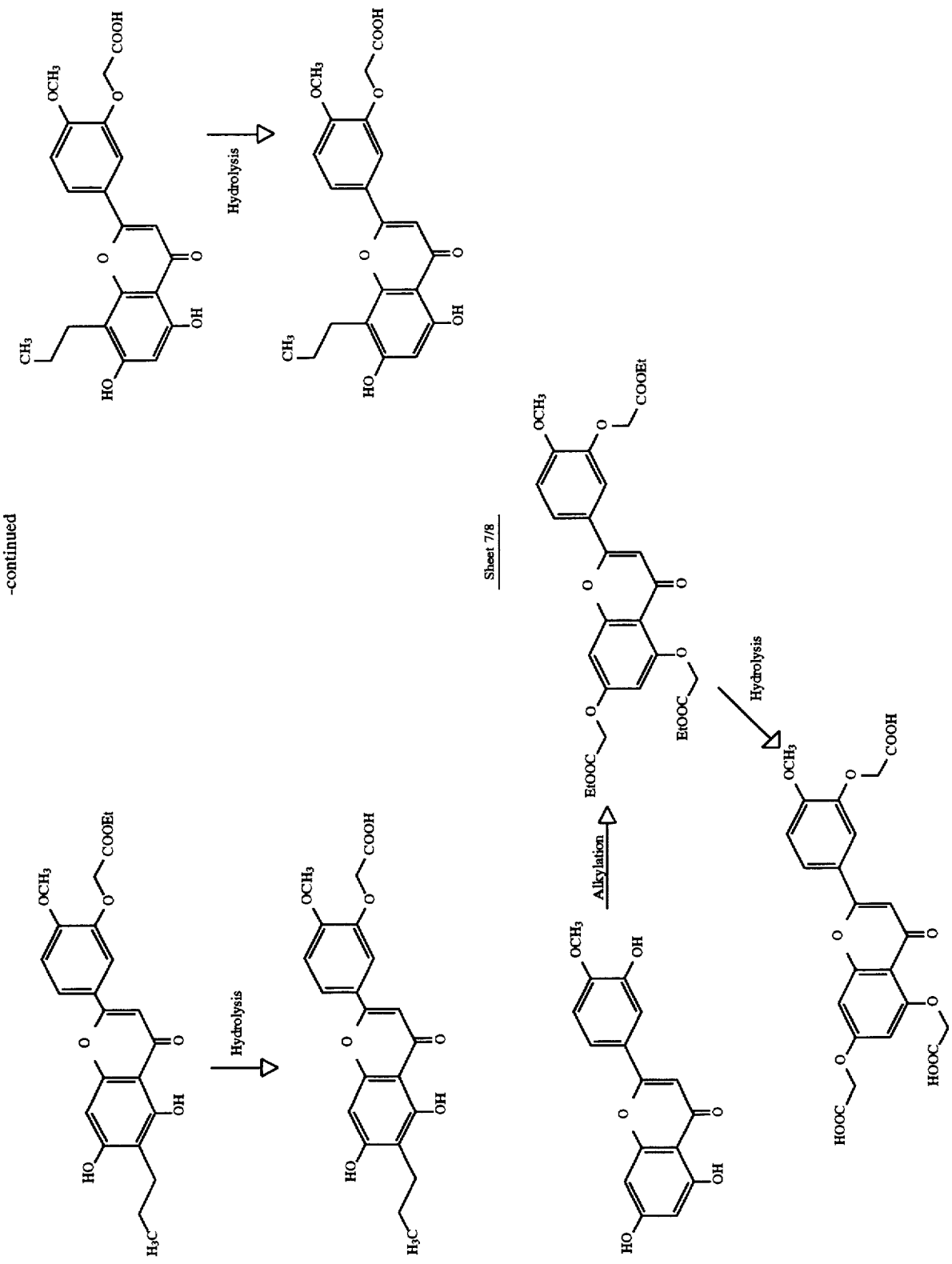

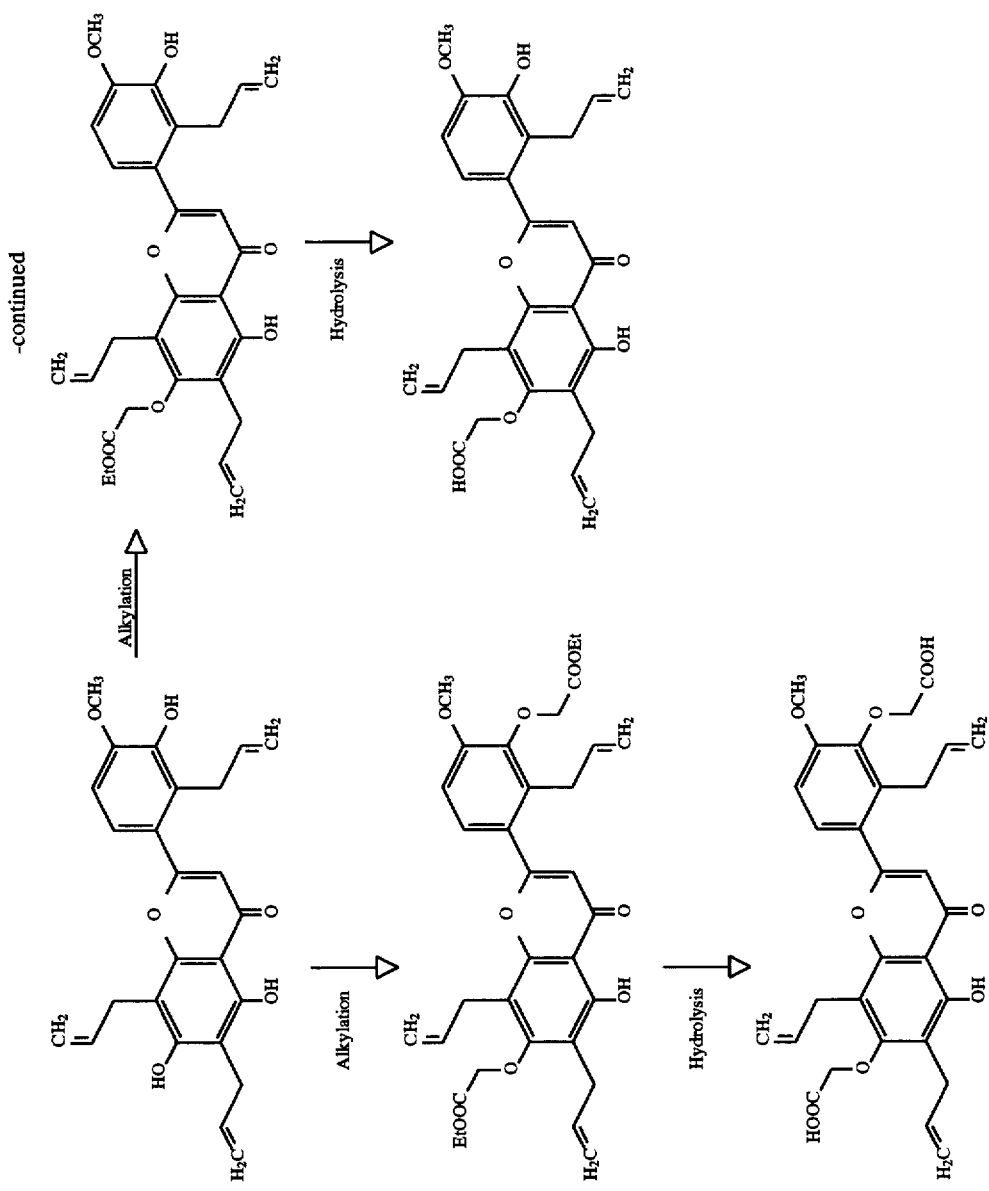

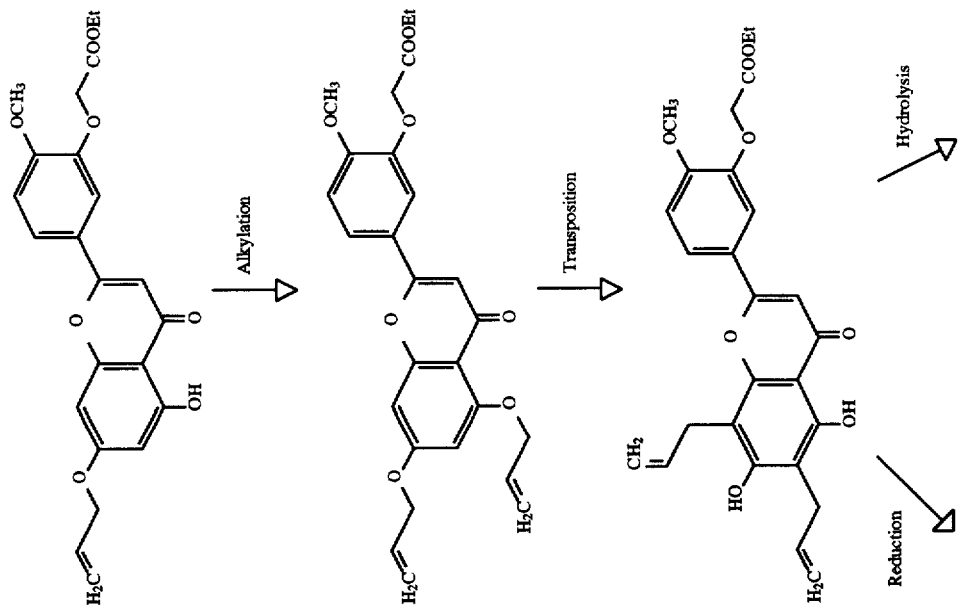

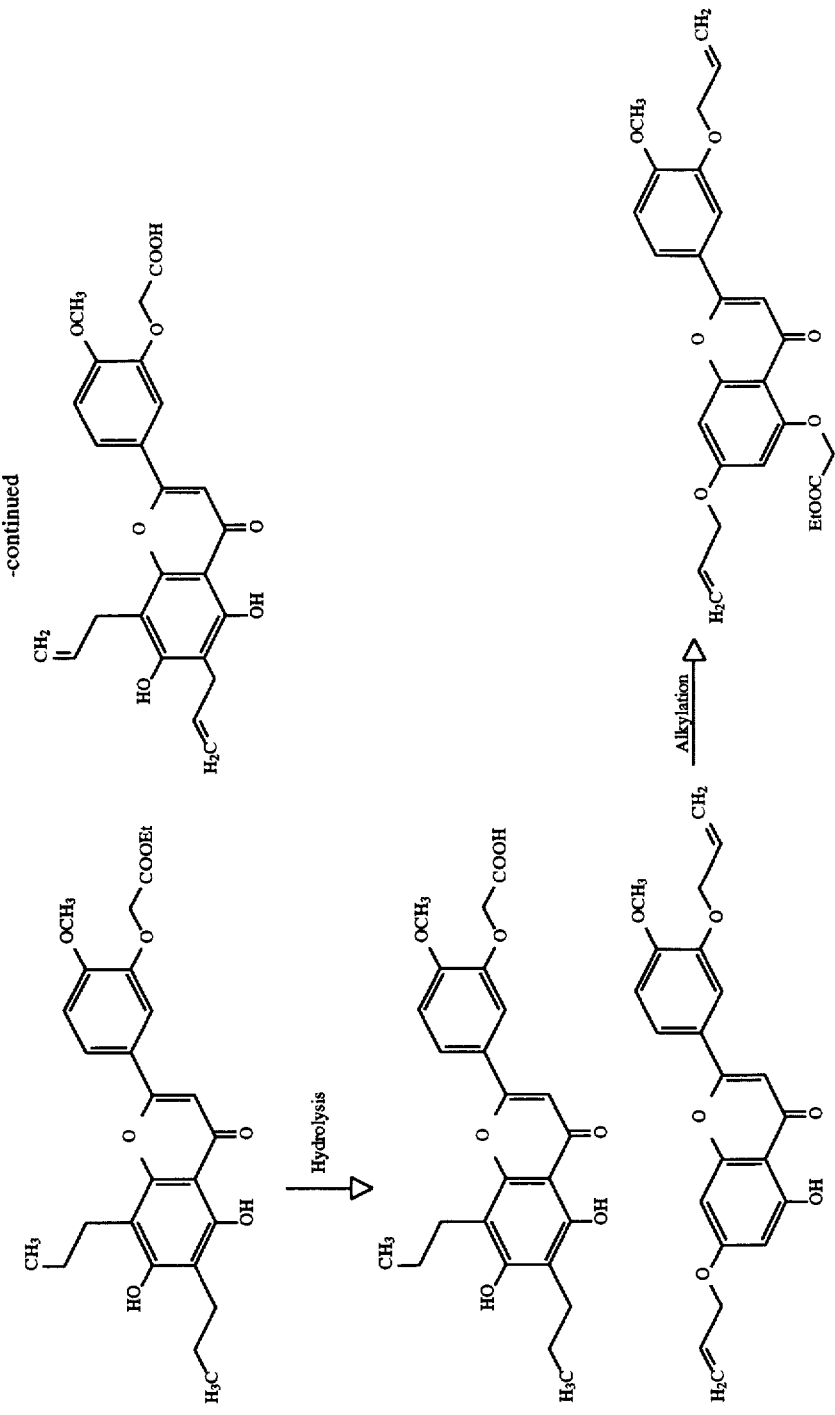

The alkylation reactions are carried out in acetone or dimethylformamide, using as base an alkali metal carbonate or hydrogen carbonate (sodium or potassium, for example), except where the alkylation relates to the group $OR_4$ in which $R_4$ represents a hydrogen atom, in which case potassium tert-butoxide or sodium hydride in a mixture of dimethylformamide and hexamethylphosphoric triamide is used. The alkylating agent used is a halo ester, glycerol-2,3-acetonide tosylate, or an alkyl or alkenyl halide.

The transposition reactions are carried out by heating the product at reflux in a solvent having a high boiling point, such as trichlorobenzene for transpositions to the ortho position, or N,N-dimethylaniline for transpositions to the para position.

The rearrangement reactions are carried out in the presence of a Lewis acid, such as aluminium chloride, in a non-reactive solvent, such as nitrobenzene or chlorobenzene.

The reduction reactions are carried out under hydrogen pressure in the presence of a catalyst, such as palladium on carbon.

The ester hydrolysis reactions are carried out by hydrolysing the compound in the presence of sodium hydroxide in a water/ethanol mixture followed by acidification, for example with dilute hydrochloric acid.

The acetonide hydrolysis reactions are carried out by heating the compound in a water/acetic acid mixture.

When the compound contains both an ester function and an acetonide function, the two hydrolyses may be carried out in succession commencing with the ester function, but without isolation of the intermediate acid-acetonide compound.

The esterification reactions are carried out by reacting the phenol in question with an acid chloride in the presence of a base, such as pyridine or triethylamine.

The following Examples illustrate the present invention.

EXAMPLE 1
7-carboxymethoxy-5-hydroxy-2-(3-hydroxy-4-methoxy-2-propylphenyl)-4H-1-benzo-pyran-4-one

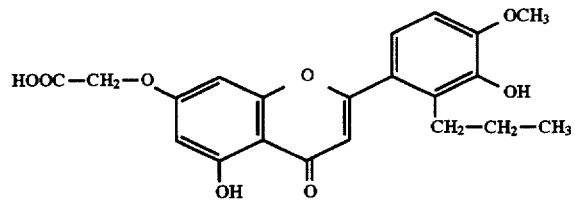

Step A: 7-ethoxycarbonylmethoxy-5-hydroxy-2-(3-allyloxy-4-methoxyphenyl)-4H-1-benzopyran-4-one α) First method 386 g of 7-ethoxycarbonylmethoxy-5-hydroxy-2-(3-hydroxy-4-methoxyphenyl)-4H-1-benzopyran-4-one (described in EP 0 319 412) are treated for 24 hours with 165 g of $K_2CO_3$ in 2300 ml of dimethylformamide. 157 g of allyl bromide are then added to the mixture and the whole is heated to 80° C. for 24 hours and then allowed to return to room temperature. The inorganic material formed is filtered off and the solvent and volatile components are removed by distillation under reduced pressure. The residual oil obtained is taken up in ethyl ether. Insoluble material is removed. The ethereal phase is concentrated to dryness by distillation and the residue obtained is recrystallised from isopropanol. 281 g of the title product of Step A (in a yield of 66 %) of a purity>95% are obtained (m.p. of an analytical sample: 171° C.).

The following compounds were prepared in the same manner:

a) 7-ethoxycarbonylmethoxy-5-hydroxy-2-[4-methoxy-3-(3-methylbut-2-enyloxy) phenyl]-4H-1-benzopyran-4-one, m.p.: 154° C., starting from 7-ethoxycarbonylmethoxy-5-hydroxy-2-(3-hydroxy-4-methoxyphenyl)-4H-1-benzopyran-4-one (see: EP 0 319 412) and

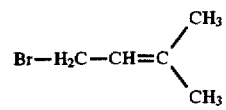

b) 5,7-diallyloxy-2-(3-ethoxycarbonylmethoxy-4-methoxyphenyl)-4H-1-benzopyran-4-one, m.p.: 105°–107° C., starting from 7-allyloxy-5-hydroxy-2-(3-ethoxycarbonylmethoxy-4-methoxyphenyl)-4H-1-benzopyran-4-one (described in the present Application), Br—$CH_2$—CH=$CH_2$ and NaH.

c) 7-(2,2-dimethyl-1,3-dioxol-4-ylmethoxy)-5-hydroxy-2-(3-ethoxycarbonyl-methoxy-4-methoxyphenyl)-4H-1-benzopyran-4-one, m.p.: 104°–105° C., starting from 7-(2,2-dimethyl-1,3-dioxol-4-ylmethoxy)-5-hydroxy-2-(3-hydroxy-4-methoxyphenyl)-4H-1-benzopyran-4-one, (see Patent Application EP 94.12783) and Br—$CH_2$—$COOC_2H_5$.

d) 7-(2,2-dimethyl-1,3-dioxol-4-ylmethoxy)-5-ethoxycarbonylmethoxy-2-(3-ethoxycarbonylmethoxy-4-methoxyphenyl)-4H-1-benzopyran-4-one, m.p.: 99° C., starting from 7-(2,2-dimethyl-1,3-dioxol-4-ylmethoxy)-5-hydroxy-2-(3-hydroxy-4-methoxyphenyl)-4H-1-benzopyran-4-one (see Patent Application EP 94.12783), Br—$CH_2$—$COOC_2H_5$ and NaH.

e) 7-(2,2-dimethyl-1,3-dioxol-4-ylmethoxy)-5-hydroxy-2-(3-ethoxycarbonyl-methoxy-4-methoxy-2-propylphenyl)-4H- 1-benzopyran-4-one, m.p.: 76° C., starting from 7-(2,2-dimethyl- 1,3-dioxol-4-ylmethoxy)-5-hydroxy-2-(3-hydroxy-4-methoxy-2-propylphenyl)-4H-1-benzopyran-4-one (see Patent Application EP 94.12783) and Br—$CH_2$—$COOC_2H_5$.

f) 7-(2,2-dimethyl-1,3-dioxol-4-ylmethoxy)-5-ethoxycarbonylmethoxy-2-(3-ethoxycarbonylmethoxy-4-methoxy-2-propylphenyl)-4H-1-benzopyran-4-one, (oil), starting from 7-(2,2-dimethyl-1,3-dioxol-4-ylmethoxy)-5-hydroxy-2-(3-hydroxy-4-methoxy-2-.propylphenyl)-4H-1-benzopyran-4-one, (see Patent Application EP 94.12783), Br—$CH_2$—$COOC_2H_5$ and NaH.

g) 6-allyl-7-(2,2-dimethyl-1,3-dioxol-4-ylmethoxy)-5-ethoxycarbonylmethoxy-2-(2-allyl-3-ethoxycarbonylmethoxy-4-methoxyphenyl)-4H-1-benzopyran-4-one, (oil), starting from 6-allyl-7-(2,2-dimethyl-1,3-dioxol-4-ylmethoxy)-5-hydroxy-2-(2-allyl-3-hydroxy-4-methoxyphenyl)-4H-1-benzopyran-4-one (see Patent Application EP 94.12783), $BrCH_2COOC_2H_5$ and NaH.

h) 6-allyl-7-(2,2-dimethyl-1,3-dioxol-4-ylmethoxy)-5-hydroxy-2-(2-allyl-3-ethoxycarbonylmethoxy-4-methoxyphenyl)-4H-1-benzopyran-4-one, (oil), starting from 6-allyl-7-(2,2-dimethyl-1,3-dioxol-4-ylmethoxy)-5-hydroxy-2-(2-allyl-3-hydroxy-4- methoxyphenyl)-4H-1-benzopyran-4-one, (see Patent Application EP 94.12783) and Br—CH$_2$—COOC$_2$H$_5$.

i) 7-allyloxy-5-hydroxy-2-(3-ethoxycarbonylmethoxy-4-methoxyphenyl)-4H-1-benzopyran-4-one, m.p.: 151° C., starting from 7-allyloxy-5-hydroxy-2-(3-hydroxy-4-methoxyphenyl)-4H-1-benzopyran-4-one (see Patent Application EP 94.12783) and Br—CH$_2$—COOC$_2$H$_5$.

j) 5,7-diethoxycarbonylmethoxy-2-(3-ethoxycarbonylmethoxy-4-methoxy-phenyl)-4H-1-benzopyran-4-one, m.p.: 150° C., starting from diosmetin, Br—CH$_2$—COOC$_2$H$_5$ and NaH.

k) 7-allyloxy-5-ethoxycarbonylmethoxy-2-(3-ethoxycarbonylmethoxy-4-methoxyphenyi)-4H-1-benzopyran-4-one, m.p.: 149°–150° C., starting from 7-allyloxy-5-hydroxy-2-(3-ethoxycarbonylmethoxy-4-methoxyphenyl)-4H- 1-benzopyran-4-one (see Patent Application EP 94.12783), Br—CH$_2$—COOC$_2$H$_5$ and NaH.

l) 6,8-diallyl-7-ethoxycarbonylmethyl-5-hydroxy-2-(2-allyl-3-ethoxycarbonyl-methoxy-4-methoxyphenyl)-4H-1-benzopyran-4-one, m.p. 98° C., starting from 6,8-diallyl-5,7-dihydroxy-2-(3-hydroxy-4-methoxyphenyl)-4H-1-benzopyran-4-one (see. Patent Application EP 94.12783) and Br—CH$_2$—COOC$_2$H$_5$.

β) Second method

The title compound of Step A was also prepared as follows: 340 g of 5,7-dihydroxy-2-(3-allyloxy-4-methoxyphenyl)-4H-1-benzopyran-4-one (see Patent Application EP 94.12783) are treated for 10 hours at 50° C. with 165 g of K$_2$CO$_3$ in 5100 ml of dimethylformamide. 200 g of ethyl bromoacetate are then added and the whole is heated to 80° C. for 15 hours and then allowed to return to room temperature. The inorganic material is filtered off and the filtrate is concentrated to dryness by distilling off the volatile elements under reduced pressure. The residue is filtered over silica using dichloromethane as eluant. The product obtained is recrystallised from isopropanol to give, in a yield of 79%, 338 g of the title compound of Step A in pure state, m.p.: 171° C.

The following compounds were prepared in the same manner:

m) 5,7-diethoxycarbonylmethoxy-2-(3-allyloxy-4-methoxyphenyl)-4H-1-benzopyran-4-one, m.p.: 120° C., starting from 5,7-dihydroxy-2-(3-allyloxy-4-methoxyphenyl)-4H-1-benzopyran-4-one, (see Patent Application EP 94.12783), BrCH$_2$COOC$_2$H$_5$ and NaH.

n) 5,7-diallyloxy-2-(4-methoxy-3-ethoxycarbonylmethoxyphenyl)-4H- 1-benzopyran-4-one, m.p. 123° C., starting from 7-allyloxy-5-hydroxy-2-(4-methoxy-3-ethoxycarbonylmethoxyphenyl)-4H-1-benzopyran-4-one (described in the present Application), allyl bromide and NaH.

o) 5-ethoxycarbonylmethoxy-7-allyloxy-2-(3-allyloxy-4-methoxyphenyl)-4H-1-benzopyran-4-one, m.p.: 107° C., starting from 7-allyloxy-5-hydroxy-2-( 3-allyloxy-4-methoxyphenyl)-4H-1-benzopyran-4-one (see Patent Application EP 94.12783), Br—CH$_2$—COOC$_2$H$_5$ and NaH.

Step B: 7-ethoxycarbonylmethoxy-5-hydroxy-2-(2-allyl-3-hydroxy-4-methoxy-phenyl)-4H- 1-benzopyran-4-one 42.6 g of 7-ethoxycarbonylmethoxy-5-hydroxy-2-(3-allyloxy-4-methoxyphenyl)-4H- 1-benzopyran-4-one (title product of Step A) are heated at reflux for 1 hour 30 in 430 ml of 1,2,4-trichlorobenzene under a nitrogen atmosphere. The reaction mixture is then brought to room temperature and diluted with 1000 ml of petroleum ether. After stirring for one hour, the precipitate is collected by filtration and then recrystallised from isopropanol. 34 g of the title compound of Step B are obtained in pure state, m.p.: 155° C. The following compounds were prepared in the same manner:

a) 5,7-diethoxycarbonylmethoxy-2-(3-hydroxy-4-methoxy-2-allylphenyl)-4H-1-benzopyran-4-one, m.p.: 125°–127° C., starting from 5,7-diethoxycarbonylmethoxy-2-(3-allyloxy-4-methoxyphenyl)-4H-1-benzopyran-4-one (described in the present Application).

b) 5-(2,2-dimethyl-1,3-dioxol-4-ylmethoxy)-7-ethoxycarbonylmethoxy-2-(2-allyl-3-hydroxy-4-methoxyphenyl)-4H-1-benzopyran-4-one, m.p.: 85° C., starting from 5-(2,2-dimethyl-1,3-dioxol-4-ylmethoxy)-7-ethoxycarbonyl-methoxy-2-(3-allyloxy-4-methoxyphenyl)-4H-1-benzopyran-4-one (described in the present Application).

c) 5,7-dihydroxy-8-allyl-2-(3-ethoxycarbonylmethoxy-4-methoxyphenyl)-4H-1-benzopyran-4-one, m.p.: 224° C.

d) 5,7-dihydroxy-6-allyl-2-(3-ethoxycarbonylmethoxy-4-methoxyphenyl)-4H-1-benzopyran-4-one, m.p.: 239° C.

The latter two compounds forming the subject of c) and d) were each obtained in the form of a mixture starting from 7-allyloxy-5-hydroxy-2-(3-ethoxycarbonylmethoxy-4-methoxyphenyl)-4H-1-benzopyran-4-one (described in the present Application), and separated by chromatography on a silica column using CH$_2$Cl$_2$/C$_2$H$_5$OH 98/2 as eluant.

e) 5,7-dihydroxy-6,8-diallyl-2-(3-ethoxycarbonylmethoxy-4-methoxy-phenyl)-4H-1-benzopyran-4-one, m.p.: 190° C., starting from 5,7-diallyl-oxy-2-(3-ethoxycarbonylmethoxy-4-methoxyphenyl)-4H- 1-benzopyran-4-one.

The transposition reaction may also be carried out to the para position, for example to prepare the following compound:

f) 7-ethoxycarbonylmethoxy-5-hydroxy-2-[5-hydroxy-4-methoxy-2-(3-methylbut-2-enyl)phenyl]-4H-1-benzopyran-4-one. 13 g of 7-ethoxycarbonylmethoxy-5-hydroxy-2-[4-methoxy-3-(3-methylbut-2-enyloxy)phenyl]-4H-1-benzo-pyran- 4-one are heated at reflux for 2 hours in 130 ml of N,N-dimethylaniline. Most of the solvent (90%) is removed by distillation under reduced pressure. The residual oil is treated at room temperature with dilute HCl and the mixture is extracted with ethyl ether. The ethereal phase is washed with water, dried and concentrated to dryness. The residue is chromatographed on silica to give, after elution with dichloromethane, 4.9 g of the expected product in the form of a practically pure oil in a 38% yield.

Step C: 7-ethoxycarbonylmethoxy-5-hydroxy-2-(3-hydroxy-4-methoxy-2-propylphenyl)-4H-1-benzopyran-4-one 21.3 g of 7-ethoxycarbonylmethoxy-5-hydroxy-2-(2-allyl-3-hydroxy-4-methoxyphenyl)-4H-1-benzopyran-4-one are dissolved in 300 ml of dimethylformamide. The solution is poured into 2 g of 10% palladium on carbon. The whole is hydrogenated at 50° C. under a pressure of 63×10$^4$ Pa until the theoretical amount of hydrogen has been absorbed. The mixture is then filtered over Millipore and the solvent is removed by distillation under reduced pressure. The crude residue (21 g) may be used as it is. An analytical sample, obtained by recrystallisation from isopropanol, melts at 138° C.

The following compounds were obtained in the same manner:

a) 7-ethoxycarbonylmethoxy-5-hydroxy-2-(4-methoxy-3-propoxyphenyl)-4H-1-benzopyran-4-one, m.p.: 157° C., starting from 7-ethoxycarbonyl-methoxy-5-hydroxy-2-(3-allyloxy-4-methoxyphenyl)-4H-1-benzopyran-4-one (described in the present Application).

b) 5,7-diethoxycarbonylmethoxy-2-(3-hydroxy-4-methoxy-2-propylphenyl)-4H-1-benzopyran-4-one, m.p.: 72° C., starting from 5,7-diethoxycarbonyl-methoxy-2-(2-allyl-3-hydroxy-4-methoxyphenyl)-4H-1-benzopyran-4-one (described in the present Application).

c) 7-ethoxycarbonylmethoxy-5-hydroxy-2-[3-hydroxy-4-methoxy-6-(3-methyl-butyl)phenyl]-4H-1-benzopyran-4-one, oil, starting from 7-ethoxycarbonyl-methoxy-5-hydroxy-2-[3-hydroxy-4-methoxy-6-(3-methylbut-2-enyl)-phenyl]-4H-1-benzopyran-4-one (described in the present Application).

d) 5,7-dihydroxy-6-propyl-2-(3-ethoxycarbonylmethoxy-4-methoxyphenyl)-4H-1-benzopyran-4-one, m.p.: 216° C., starting from 5,7-hydroxy-6-allyl-2-[3-ethoxycarbonylmethoxy-4-methoxyphenyl)-4H-1-benzopyran-4-one (described in the present Application).

e) 5,7-dihydroxy-8-propyl-2-(3-ethoxycarbonylmethoxy-4-methoxyphenyl)-4H-1-benzopyran-4-one, m.p.: 190° C., starting from 5,7-dihydroxy-8-allyl-2-(3-ethoxycarbonylmethoxy-4-methoxyphenyl)-4H-1-benzopyran-4-one (described in the present Application).

f) 5,7-dihydroxy-6,8-dipropyl-2-(3-ethoxycarbonylmethoxy-4-methoxy-phenyl)-4H-1-benzopyran-4-one, m.p.: 205° C., starting from 5,7-di-hydroxy-6,8-diallyl-2-(3-ethoxycarbonylmethoxy-4-methoxyphenyl)-4H-1-benzopyran-4-one (described in the present Application).

Step D: Title product of Example 1

10.7 g of 7-ethoxycarbonylmethoxy-5-hydroxy-2-(3-hydroxy-4-methoxy-2-propyl-phenyl)-4H-1-benzopyran-4-one are heated at reflux for 1 hour in a mixture of 44 ml of N sodium hydroxide solution and 88 ml of ethanol. The ethanol is then removed by distillation and the aqueous mixture is filtered over a Millipore filter with the application of heat. The basic filtrate is then acidified to pH 1 with a N HCl solution. The precipitate formed is collected by filtration, dried and then recrystallised from a water/acetone mixture to yield 9 g of the title compound of Example 1 in pure state, m.p.: 251° C.

The following acids were prepared in the same manner starting from corresponding ethyl esters all included in the present Application:

a) 7-carboxymethoxy-5-hydroxy-2-(3-allyloxy-4-methoxyphenyl)-4H- 1-benzopyran-4-one, m.p.: 253°–255° C.

b) 7-carboxymethoxy-5-hydroxy-2-(4-methoxy-3-propoxyphenyl)-4H-1-benzopyran-4-one, m.p.: 259° C.

c) 7-carboxymethoxy-5-hydroxy-2-(2-allyl-3-hydroxy-4-methoxyphenyl)-4H-1-benzopyran-4-one, m.p.: 264° C.

d) 5,7-dicarboxymethoxy-2-(2-allyl-3-hydroxy-4-methoxyphenyl)-4H- 1-benzopyran-4-one, m.p.: 247° C.

e) 5,7-dicarboxymethoxy-2-(3-hydroxy-4-methoxy-2-propylphenyl)-4H-1-benzopyran-4-one, m.p.: 255° C.

f) 7-carboxymethoxy-5-hydroxy-2-[3-hydroxy-4-methoxy-6-(3-methybut-2-enyl)phenyl]-4H-1-benzopyran-4-one, m.p.: 210° C.

g) 5,7-dicarboxymethoxy-2-(3-carboxymethoxy-4-methoxyphenyl)-4H-1-benzopyran-4-one, m.p.: 300° C.

h) 6,8-diallyl-7-carboxymethoxy-5-hydroxy-2-(2-allyl-3-hydroxy-4-methoxy-phenyl)-4H-1-benzopyran-4-one, m.p.: 209° C.

i) 5,7-dihydroxy-6,8-dipropyl-2-(3-carboxymethoxy-4-methoxyphenyl)-4H-1-benzopyran-4-one, m.p.: 232° C.

j) 7-carboxymethoxy-6,8-diallyl-5-hydroxy-2-(2-allyl-3-carboxymethoxy-4-methoxyphenyl)-4H-1-benzopyran-4-one, m.p.: 91° C.

k) 5,7-dihydroxy-6-propyl-2-(3-carboxymethoxy-4-methoxyphenyl)-4H-1-benzopyran-4-one, m.p.: 259° C.

l) 5,7-dihydroxy-8-propyl-2-(3-carboxymethoxy-4-methoxyphenyl)-4H- 1-benzopyran-4-one, m.p.: 250° C.

m) 8-allyl-5,7-dihydroxy-2-(3-carboxymethoxyphenyl)-4H-1-benzopyran-4-one, m.p.: 223° C.

n) 6-allyl-5,7-dihydroxy-2-(3-carboxymethoxy-4-methoxyphenyl)-4H-1-benzopyran-4-one, m.p.: 265° C.

o) 6,8-diallyl-5,7-dihydroxy-2-(3-carboxymethoxy-4-methoxyphenyl)-4H-1-benzopyran-4-one, m.p.: 200° C.

p) 7-carboxymethoxy-5-hydroxy-2-[2-(3-methyl-n-butyl)-5-hydroxy-4-meth-oxyphenyl]-4H-1-benzopyran-4-one, m.p.: 159° C.

Those acids may be converted into the sodium salt, for example as follows:

q) the sodium salt of 7-carboxymethoxy-5-hydroxy-2-(2-allyl-3-hydroxy-5-methoxyphenyl)-4H- 1-benzopyran-4-one: 3.98 g of 7-carboxymethoxy-5-hydroxy-2-(2-allyl-3-hydroxy-4-methoxy-phenyl)-4H-1-benzopyran-4-one are dissolved in 10 ml of N sodium hydroxide in 390 ml of water. The solution is rendered clear by filtration over a Millipore filter. The filtrate is concentrated to dryness by distilling off the water under reduced pressure, and the residue is recrystallised from a water/ethanol mixture. 3.5 g of the expected sodium salt are obtained, m.p.>260° C.

The hydrolysis may also simultaneously apply to ester and acetonide, such as, for example, for the preparation of the following compound:

r) 7-(2,3-dihydroxypropoxy)-5-hydroxy-2-(3-carboxymethoxy-4-methoxy-2-propylphenyl)-4H-1-benzopyran-4-one: 5.42 g of 7-(2,2-dimethyl-1,3-dioxol-4-yl)methoxy-5-hydroxy-2-(3-ethoxycarbonylmethoxy-4-methoxy-2-propylphenyl)-4H-1-benzopyran-4-one are heated at reflux for 1 hour in a mixture of 12 ml of N sodium hydroxide and 80 ml of ethanol. 10 ml of water and 32 ml of acetic acid are then added to the mixture, and the whole is heated at reflux until dissolution is complete (approximately 15 to 30 minutes), and then allowed to return to room temperature. The resulting precipitate is filtered off, washed with water and then recrystallised from acetone. 3 g of the expected compound are obtained in pure state, m.p.: 135°–145° C.

The following compounds were prepared in the same manner:

s) 7-(2,3-dihydroxypropoxy)-5-hydroxy-2-(3-carboxymethoxy-4-hydroxy-phenyl)-4H-1-benzopyran-4-one, m.p.: 217° C., starting from 7-(2,2-dimethyl-1,3-dioxol-4-ylmethoxy)-5-hydroxy-2-(3-ethoxycarbonylmethoxy- 4-methoxyphenyl)-4H-1-benzopyran-4-one (described in the present Application).

t) 5-carboxymethoxy-7-(2,3-dihydroxypropoxy)-2-(3-carboxymethoxy-4-methoxyphenyl)-4H-1-benzopyran-4-one, m.p.: of the corresponding dihydrate: 161° C., starting from 7-(2,2-dimethyl-1,3-dioxol-4-ylmethoxy)-5-ethoxycarbonylmethoxy-2-(3-ethoxycarbonylmethoxy-4-methoxyphenyl)-4H-1-benzopyran-4-one (described in the present Application).

u) 5-carboxymethoxy-7-(2,3-dihydroxypropoxy)-2-(3-carboxymethoxy-4-methoxy-2-propylphenyl)-4H-1-benzopyran-4-one, m.p.>250° C., starting from 7-(2,3-dimethyl-1,3-dioxol-4-ylmethoxy)-5-ethoxycarbonylmethoxy-2-(3-ethoxycarbonylmethoxy-4-methoxy-2-propylphenyl)-4H-1-benzopyran-4-one (described in the present Application).

v) 6-allyl-7-(2,3-dihydroxypropoxy)-5-hydroxy-2-(2-allyl-3-carboxymethoxy-4-methoxyphenyl)-4H-1-benzopyran-4-one, m.p.: 139°–140° C., starting from 6-allyl-7-(2,2-dimethyl-1,3-dioxol-4-ylmethoxy)-5-hydroxy-2-(2-allyl-3-ethoxy-carbonylmethoxy-4-methoxyphenyl)-4H-1-benzopyran-4-one (described in the present Application).

w) 7-carboxymethoxy-5-(2,3-dihydroxypropoxy)-2-(2-allyl-3-hydroxy-4-methoxyphenyl)-4H-1-benzopyran-4-one, m.p.: 236° C., starting from 5-(2,2-dimethyl-1,3-dioxol-4-ylmethoxy)-7-ethoxycarbonylmethoxy-2-(2-allyl-3-hydroxy-4-methoxyphenyl)-4H-1-benzopyran-4-one (described in the present Application).

Those acids may also be converted into the sodium salt, for example as follows:

x) the sodium salt of 7-(2,3-dihydroxypropoxy)-5-hydroxy-2-(3-carboxy-methoxy-4-methoxy-2-propylphenyl)-4H-1-benzopyran-4-one: 4.74 g of 7-(2,3-dihydroxypropoxy)-5-hydroxy-2-(3-carboxymethoxy-4-methoxy-2-propylphenyl)-4H-1-benzopyran-4-one are dissolved in 10 ml of N sodium hydroxide and 200 ml of water. The mixture is filtered over a Millipore filter. The filtrate is concentrated to dryness. The residue obtained is recrystallised from acetone to yield 4 g of the expected sodium salt, m.p.: 245°–246° C.

By proceeding in the same manner it is possible to obtain a calcium salt of a diacid, such as, for example:

y) the calcium salt of 5-carboxymethoxy-7-(2,3-dihydroxypropoxy)-2-(3-carboxymethoxy-4-methoxy-2-propylphenyl)-4H-1-benzopyran-4-one, which, recrystallised from a water/acetone mixture, melts above 250° C.

EXAMPLE 2

Pharmacological study

1/Anti-hypermeability activity

The anti-hypermeability activity was determined by the effect of the compounds of the invention on the extravasation of FITC-dextran in the microcirculation of the hamster cheek pouch. The hamster cheek pouch is an experimental model that allows the quantitative study of the permeability of macromolecules using dextran labelled with fluorescein (FITC-dextran).

The experiments were carried out on male hamsters weighing from 85 to 120 g. The animals are anaesthetised with sodium pentobarbital (60 mg/kg, i.p.). During the experiment, the anaesthesia is maintained using ($\alpha$-chloralose (100 mg/kg) introduced through a catheter into the femoral artery. The animals breathe spontaneously through a tracheal cannula and the body temperature is maintained at 37.5° C. using a heating pad controlled by a rectal thermistor.

After the initial anaesthesia, the cheek pouch is prepared in accordance with the method described by Duling (Microvasc. Res., 5, 423–429, 1973) and Svensjö et al. (Uppsala. J. Med. Sci., 83, 71–79, 1978). The preparation is set up in an experimental bath and superfused at 6 ml/min with a physiological solution containing Hepes. The temperature of the physiological solution is maintained at 36.5° C. and a stream of gas (5% $CO_2$—95% $N_2$) is applied above the experimental bath in order to maintain the $pO_2$ level in the solution between 12 and 15 mmHg and the pH at 7.4.

Thirty minutes after setting up the preparation, FITC-dextran (150,000 dalton, 50 mg/ml) is administered to the animal by the intravenous route at a dose of 250 mg/kg. The preparation is observed by the "intravital microscopy" method under UV light using a Leitz Ortholux II microscope.

After the injection of FITC-dextran, the preparation is subjected to a local administration of an agent that induces permeability: histamine at a concentration of $2\times10^{-6}$M.

The administration of those agents and the period of ischaemia cause "leaks" (visible as small fluorescent spots) throughout the preparation. The number of leaks is determined at several intervals (from 2 to 30 min) after the administration of histamine and is expressed as the number of leaks per $cm^2$. The preparations are subjected several times (separated by at least 30 minutes) to a local administration of histamine.

Two types of study were carried out in order to determine the activity per os of the compounds of the present invention.

The animals are treated by force-feeding, thirty minutes before anaesthesia, with a dose of 100 mg/kg of one of the compounds of the invention suspended in gum arabic. The dose of the compound is contained in 0.2 ml. The control animals receive a force-feed of 0.2 ml of gum arabic (placebo). The compounds of the invention, administered at 100 mg/kg p.o. to the hamster, significantly decrease (t-test; *p<0,05) in a lasting manner the extravasation of macromolecules caused by the histamine in the microcirculation. The results obtained with the histamine, 3 hours after administration of the products, are summarised in Table 1. The results are superior to those obtained under the same operating conditions with the reference substance troxerutin.

TABLE 1

Influence of the compounds of the invention on the extravasation of FITC-dextran in the hamster cheek pouch after treatment per os (100 mg/kg)

| Products | Number of leaks per cm² | |
|---|---|---|
|  | Untreated | 3 h after treatment |
| Compound of Example 1 | 343 | 251 |
| Compound of Example 1 Step D, b) | 394 | 295 |
| Compound of Example 1 Step D, c) | 343 | 227 |
| Compound of Example 1 Step D, d) | 374 | 313 |
| Compound of Example 1 Step D, e) | 374 | 287 |
| Compound of Example 1 Step D, g) | 374 | 294 |
| Compound of Example 1 Step D, m) | 368 | 324 |
| Compound of Example 1 Step D, o) | 368 | 191 |
| Compound of Example 1 Step D, p) | 443 | 363 |
| Compound of Example 1 Step D, s) | 443 | 354 |
| Compound of Example 1 Step D, u) | 374 | 239 |
| Compound of Example 1 Step D, v) | 374 | 190 |

We claim:

1. A compound selected from the group consisting of: diosmetin acids and esters of formula (I):

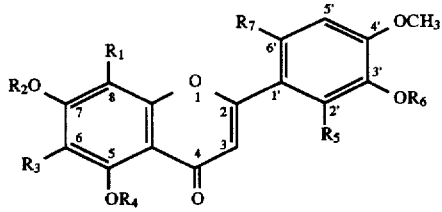

wherein:

$R_2$, $R_4$ and $R_6$, which are identical or different, are each selected from the group consisting of hydrogen, alkyl having 1 to 5 carbon atoms inclusive in straight or branched chain,

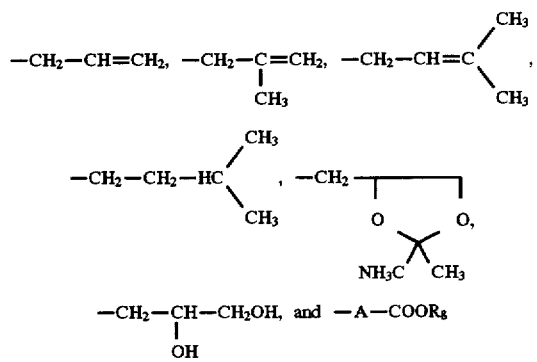

wherein:

A is selected from the group consisting of straight hydrocarbon chains having 1 to 3 carbon atoms inclusive, unsubstituted or substituted by a substituent selected from the group consisting of methyl and hydroxy, and $R_8$ is selected from the group consisting of hydrogen and alkyl having 1 to 5 carbon atoms inclusive, and at least one of $R_2$, $R_4$, and $R_6$ being —A—COOR$_8$, and $R_3$ and $R_5$, which are identical or different, are each selected from the group consisting of hydrogen,

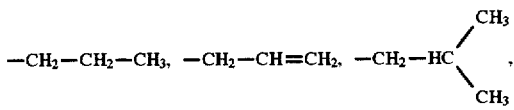

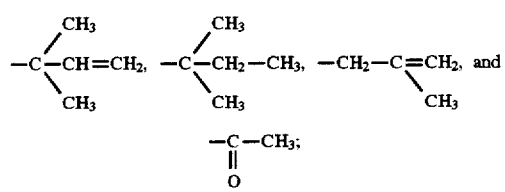

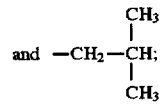

and $R_1$ and $R_7$, which are identical or different, are each selected from the group consisting of hydrogen,

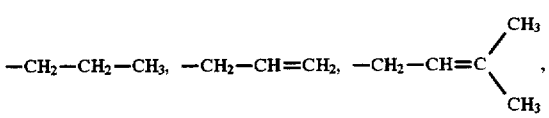

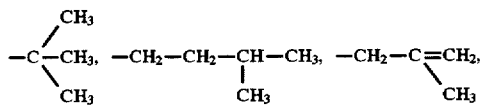

$$\text{and } -CH_2-\underset{\underset{CH_3}{|}}{CH};$$

with the proviso that:

if 1 or 2 of the substituents $R_2$, $R_4$, and $R_6$ represent(s) —A—COOR$_8$ wherein A and $R_8$ are as defined above, then at least one of the remaining substituents $R_1$ to $R_7$ does not represent hydrogen;

enantiomers thereof, where they exist, and the physiologically-tolerable salts thereof with a base.

2. A compound of claim 1 which is 7-carboxymethoxy-5-hydroxy-2-(3-hydroxy-4-methoxy-2-propylphenyl)-4H-1-benzopyran-4-one.

3. A compound of claim 1 which is 7-carboxymethoxy-5-hydroxy-2-(4-methoxy-3-propoxyphenyl)-4H-1-benzopyran-4-one.

4. A compound of claim 1 which is 7-carboxymethoxy-5-hydroxy-2-(2-allyl-3-hydroxy-4-methoxyphenyl)-4H-1-benzopyran-4-one.

5. A method for treating a living animal body afflicted with a condition selected from chronic venous insufficiency, a disorder involving hyperpermeability, or inflammation, comprising the step of administering to the said living animal body an amount of a compound of claim 1 which is effective for the alleviation of said condition.

6. A pharmaceutical composition useful for treating hypermeability or inflammation comprising as active ingredient a compound according to claim 1, in admixture or association with a pharmaceutically-acceptable excipient.

* * * * *

UNITED STATES PATENT AND TRADEMARK OFFICE
CERTIFICATE OF CORRECTION

PATENT NO. : 5,792,789
DATED : August 11, 1998
INVENTOR(S) : M. Wierzbicki, M.F. Boussard, T. Verbeuren, M.O. Vallex Page 1 of 3

It is certified that error appears in the above-indentified patent and that said Letters Patent is hereby corrected as shown below:

Column 1, line 21: The formula should read:

Page 1, line 9

Column 1, line 28: This formula should read:

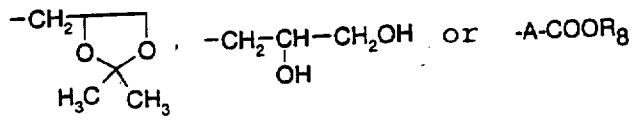

Page 1, line 10

Column 13, line 1: The first formula should read:

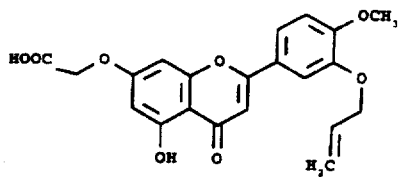

Sheet 4/8, 1st formula on left

UNITED STATES PATENT AND TRADEMARK OFFICE
CERTIFICATE OF CORRECTION

PATENT NO. : 5,792,789
DATED : August 11, 1998
INVENTOR(S) : M. Wierzbicki, M.F. Boussard, T. Verbeuren, M.O. Vallex It is certified that error appears in the above-indentified patent and that said Letters Patent is hereby corrected as shown below:

Column 20: The last formula should read:

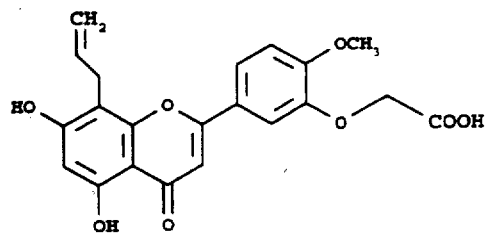

Sheet 6/8, 5th formula

Column 34, line 35: "-5-hydroxy-4-meth-oxyphenyl]"
   should read:  -- -5-hydroxy-4-methoxyphenyl] --.
   Page 14, line 5

UNITED STATES PATENT AND TRADEMARK OFFICE
CERTIFICATE OF CORRECTION

PATENT NO. : 5,792,789
DATED : August 11, 1998
INVENTOR(S) : M. Wierzbicki, M.F. Boussard, T. Verbeuren, M.O. Vallex Page 3 of 3

It is certified that error appears in the above-indentified patent and that said Letters Patent is hereby corrected as shown below:

Column 37, line 58: The last formula in this line should read:

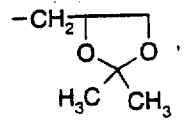

Page 20, line 9, 5th formula

Signed and Sealed this

First Day of August, 2000

Q. TODD DICKINSON

*Attest:*

*Attesting Officer*      *Director of Patents and Trademarks*